United States Patent
Iqbal et al.

(10) Patent No.: US 6,861,219 B2
(45) Date of Patent: Mar. 1, 2005

(54) PREFERENTIAL DISPLAY

(75) Inventors: Shahzi Iqbal, San Ramon, CA (US);
Robert Chin, Austin, TX (US)

(73) Assignee: Genexpress Informatics, Inc., Austin, TX (US)

( * ) Notice: Subject to any disclaimer, the term of this patent is extended or adjusted under 35 U.S.C. 154(b) by 76 days.

(21) Appl. No.: 09/961,089

(22) Filed: Sep. 24, 2001

(65) Prior Publication Data

US 2003/0207269 A9 Nov. 6, 2003

Related U.S. Application Data

(60) Provisional application No. 60/234,751, filed on Sep. 25, 2000.

(51) Int. Cl.$^7$ ............................. C12Q 1/68; C12P 19/34
(52) U.S. Cl. ....................... 435/6; 435/91.1; 435/91.2; 435/91.51; 435/183; 536/23.1; 536/23.5; 536/23.6; 536/24.1; 536/24.33
(58) Field of Search ......................... 435/6, 91.1, 91.2, 435/91.51, 183; 536/23.1, 23.5, 23.6, 24.1, 24.33

(56) References Cited

U.S. PATENT DOCUMENTS

| | | | | |
|---|---|---|---|---|
| 5,525,471 A | * | 6/1996 | Zeng ............................... | 435/6 |
| 5,712,127 A | | 1/1998 | Malek et al. ............. | 435/91.21 |
| 5,759,780 A | | 6/1998 | Parker et al. .................... | 435/6 |
| 5,804,382 A | * | 9/1998 | Sytkowski et al. ............. | 435/6 |
| 5,935,788 A | * | 8/1999 | Burmer et al. .................. | 435/6 |
| 5,958,738 A | | 9/1999 | Linemann et al. .......... | 435/91.2 |
| 6,017,701 A | | 1/2000 | Sorge et al. .................... | 435/6 |
| 6,060,245 A | | 5/2000 | Sorge et al. .................... | 435/6 |
| 6,342,376 B1 | * | 1/2002 | Kozian et al. ............. | 435/91.2 |

* cited by examiner

*Primary Examiner*—Carla J. Myers
*Assistant Examiner*—Alexander H. Spiegler
(74) *Attorney, Agent, or Firm*—Toler & Larson & Abel L.L.P.

(57) ABSTRACT

There is a tremendous need for high throughput gene expression technology which can efficiently and cheaply identify and accurately isolate different genes expressed between diseased and normal tissues for use in discovering new drugs. The present invention utilizes a combination of biomolecular chemistry methods to eliminate/degrade redundant sequences and fluorescence dye assay to identify these unique sequences from two cell or tissue populations. cDNA from normal or diseased cells or tissues are hybridized with the RNA of the complement normal or diseased cells or tissues. The hybridized cDNA/RNA is incubated with exonucleases, resulting in degradation of all but the single stranded RNA and DNA. RNA are then eliminated using RNase and the remaining DNA which are unique to the sample are amplified. This technique may be used to isolate differentially expressed genes or gene fragments and will provide a means to isolate and identify medium to low gene expressions that may otherwise be buried under gene "Noise".

18 Claims, 2 Drawing Sheets

PREFERENTIAL DISPLAY

RELATED APPLICATIONS

This application claims priority of U.S. patent application, Ser. No., 60/234,751, filed Sep. 25, 2000 entitled: "Preferential Display", and is incorporated herein by reference in entirety.

TECHNICAL FIELD OF INVENTION

This invention, in general, relates to analysis of gene expression. More specifically, this invention relates to the preferential display of differences between two gene expression samples.

BACKGROUND OF INVENTION

Methods for assaying gene expression can be classified into two major types: open methods, which do not require prior knowledge of the genes being measured, and closed methods, which measure expression levels of already collected clones or sequences. Some expression analysis techniques can only measure on a gene-by-gene basis while others can assay multiple genes simultaneously. Finally, some methods can directly measure differential expression between two samples and some examine expression levels from one sample at a time, followed by computation based comparisons. Understanding differences between these methods is essential for choosing the best technology for a given application. Regardless of the methods chosen researchers must identify or access through databases vast quantities of expression information to find the actual cause and effect on the gene expression.

The history of gene expression analysis began when laboratory methods were developed to examine expression of individually known genes. The northern blot technique, introduced in 1977, hybridizes labeled DNA or RNA of known genes to RNA blots. The resulting expression patterns of mRNA transcripts were then read. This technique is still widely used to confirm the results of other types of gene expression studies. In 1977, another method was published that protects a DNA-labeled probe against degradation by the single-stranded nuclease SI if the probe is annealed to an RNA. Ten years later, RNase protection assays were developed to detect the expression of specific, previously characterized RNAs and to compare their levels of expression. With this technique, a specific labeled cDNA forms a hybrid with its corresponding mRNA. When exposed to a single-strand-specific nuclease, the hybrids resist degradation and can be detected using gel electrophoresis. A later approach, differential plaque-filter hybridization, can detect differences in the expression of cloned cDNA between two samples.

In 1993, subtractive hybridization techniques became available for constructing subtractive cDNA libraies. This methodology hybridizes cDNA from one pool to mRNA from another. Then, cDNA libraries are constructed from the transcripts that are not hybridized, these being used to identify specific mRNAs. A modification of this technique, representational difference analysis (RDA), also uses preferential amplification of non-subtracted fragments. In RDA, "representations" or simplified versions of the genomes being studied (amplicons) are created using restriction digestion This method was first developed to examine the differences between genomes, but has proven useful for cloning differentially expressed genes. From this method, suppressive subtractive hybridization (SSH) was derived, which enables further suppression amplification of non-subtracted fragments. SSH combines normalization (equalizing the abundance of cDNAs within the target population) and subtraction (excluding the common sequences between the target and driver populations) in a single procedure. Results from both RDA and SSH should be validated using other methods.

Early gene expression methods, such as those already mentioned, are relatively small-scale techniques. They either focus on measuring mRNA expression levels for individual well-characterized genes, or use in vitro nuclear "run-on" transcription assays to determine the transcriptional profiles of several active genes simultaneously. They are therefore inadequate for conducting large-scale screening and developing expression profile patterns for tissues or cells (the basic requirements for efficient pharmaceutical research). Thus, several newer methods for high-throughput screening (HTS) have been developed over the past decade, including differential display, expressed sequence tag (EST) methodology and many array techniques. Collectively, they have made it possible to identify the expression levels of novel genes and characterize them., correlate mRNA expression patterns in many tissue types with disease states, identify side effects of current and experimental treatments, and determine the effects of compounds on non-target tissues.

Differential display of eukaryotic mRNA, first reported in 1992, was a major advance in the comparison of gene expression differences between cells or tissues. Encompassing the use of either arbitrarily or specifically primed PCR, it is perhaps the most widely used method involving gel electrophoresis for comparing gene expression. Both methods amplify partial cDNAs from subsets of mRNA samples by using reverse transcription and PCR. These short cDNA fragments are then typically displayed on polyacryl-amide gels. Differential display can simultaneously measure both up- and down-regulation across tens of samples.

Originally, this method used an oligo(dT) primer with an anchor of one or two bases at the 39 terminal. Reverse transcription and denaturation were followed by arbitrary priming on the resulting first strand of cDNA. A series of products were then derived from the 39 end of the mRNAs by using PCR with the original primer (a radiolabeled nucleotide) and a set of short, random decamer primers. Each random primer annealed to the mRna at a different position relative to the anchor primer. Products showing significant differential expression were sequenced after size fractionation of the PCR sample using denaturing gel electrophoresis, generally after overnight autoradiographic exposure.

EST methodology can determine the expression profile of an entire cell or tissue under analysis. During the 1990s, EST methodology played the largest role in increasing the catalog of known genes. Using this approach cDNA clones are randomly picked and a single pass of sequencing is performed from one or both ends of each clone. Subsequent comparison with existing sequence databases immediately identifies novel sequences. Measuring how often a given sequence appears in a (representational) library enables the estimation of expression levels for each gene.

Although this method can accurately identify the presence of a proportion of genes relatively low sampling (typically 5,00010,000 sequences are generated from a tissue containing >20,000 distinct transcript types) makes it difficult to measure abundance of expression or to identify differentially expressed genes except where genes are highly up- or down-regulated.

Serial analysis of gene expression (SAGE) can potentially tag and analyze all transcripts in a given cell population or tissue. It has been used to successfully compare expression profiles between normal and cancerous cells, and detect p53 levels prior to apoptosis. In theory, SAGE is an "open"0 system. However, in practice, the short length of the tags means that it is most useful for expression profiling of fully sequenced genes. Thus, the value of this technique might increase as the Human Genome Project progresses.

This method uses two samples that are ligated and tagged with separate primers and then amplified. Subsequently, the primers are removed, revealing sticky ends that form concatemers. The concatemers are both cloned into a vector, with sequence information for the two different cDNA tags contained between anchoring sites. This cloning and sequencing process is time-consuming, as it must be performed for each sample and followed by extensive computational analysis.

The public EST efforts, spearheaded by sequencing work at Washington University (St. Louis, Mo., USA) and the arraying efforts of the IMAGE Consortium (founded by researchers at the Lawrence Livermore National Laboratory, Columbia University, National Institutes of Health and Centre National de la Recherche Scientifique), have made sequences and clones for more than one million cDNA clones publicly available. A network of five distributors across the globe supplies researchers with clones and related research services, such as sets of sequence-verified cDNA clones spotted onto nylon membranes. As standard laboratory protocols can be used and the filters are commercially available at a relatively modest cost, they are a popular forerunner to microarrays. Hybridization of radioactively labeled complex RNA to these membranes yields signals for moderately and abundantly expressed genes and, depending on several factors, some of the less abundant transcripts. Thus, differential expression is best measured using genes that are moderately expressed in at least one of the two (or more) states under study.

DNA microarrays measure expression by using templates containing hundreds or thousands of probes that are exposed simultaneously to a target sample. They make it possible to systematically survey DNA and RNA variation for the first time and are becoming a standard tool for drug discovery and evaluation. Microarray techniques are so powerful that their uses are often limited largely by the challenge of managing and analyzing the data they generate. DNA microarray technology evolved from a paper published in 1975 by E. M. Southern (the originator of the Southern blot), who showed how a solid support could be used to examine nucleic acids. This was advanced by the development of non-porous solid supports, Icading to miniaturization and the use of fluorescence-based detection methods. The two main types of templates are long DNA fragments (over 100 base pairs) and oligonuclotides (generally 1825 mers). Microarrays are expensive, although efficiencies should improve and costs should drop dramatically in the next couple of years, enabling these tools to become accessible to most research laboratories. Besides cost, microarrays are limited by the fact that they can only probe genes for which clones or sequences are already available. Further-more, their accuracy can be limited by the purity of the RNA and the quantity of RNA for each hybridization.

By understanding gene expression patterns, researchers can gain information that can link sites of expression, bio-chemical pathways, and normal or pathological functions in organs and whole organisms. Because of their speed and breadth, microarrays should impact genetic profiling in several ways: Accelerate the understanding of the molecular basis of disease or environmental stresses, Improve knowledge of model systems, Explore pathogens, pathogenic, environmental (microgravity) reactions in terms of gene expression, Pinpoint new molecular level explanations to environmental effects, and Examine efficacy and toxicity responses to environmental or other external simulates.

Microarrays have already determined bow several important genes arm abnormally regulated in disease. For example, a microarray of approximately 100 genes that have a role in inflammation was used to examine rheumatoid tissue. This revealed upregulation of the genes encoding interleukin-6 and several matrix metalloproteinases. In another instance, a novel gene involved in promoting tumors was discovered by using a 1000-element micro-array of unknown cDNAs to examine how treatment with phorbol testers affects expression levels. Microarrays should provide more detailed knowledge about pathogens by systematically examining every gene in a microbe to uncover the overall expression pattern. In addition, microarray will continue to contribute to the understanding of responses to drug treatments. For example, a recent study used microarrays to measure the effects of kinase inhibitors on the entire yeast genome by measuring changes in mRNA levels before and after treatment. In another example, microarray studies of yeast cells showed that the immunosuppressive drug FK506 had the same effect on gene expression level patterns as ablation of the gene that FK506 suppresses. Furthermore, this study showed that, in the absence of this gene, FK506 affected expression levels in other ways. This suggests that the drug might have more than one target. Microarrays are also proving useful in the determination of drug toxicity.

Expression profiling using cDNA microarrays begins by arraying many gene specific amplicons derived from the cDNA clones onto a single matrix. Using two-color hybridization, cDNA representations of total RNA pools are created from test and reference cells, fluorescently tagged with two different colors, then mixed together before being hybridized to the matrix. For each transcript, the resulting fluorescence signals reflect the difference in abundance between the two samples. Two-color hybridizations provide rapid comparisons between the two samples, but they do not measure the absolute levels of gene expression for either sample. By contrast, one-color hybridization is slightly slower, as hybridizations of the two samples must be performed separately to reach meaningful comparisons. However, each one-color hybridization measures absolute levels of gene expression rather than comparative levels. After these actual levels are recorded in databases, they can be compared with levels from other samples without the need to perform comparative experiments. Although performing 1000 two-color hybridizations results in 1000 pair-wise comparisons, conducting 1000 one-color hybridizations yields almost half-a-million pair-wise comparisons, as the absolute values of one-color hybridizations can be evaluated against each other.

Using either the one- or two-color methods, microarray experiments must be performed repeatedly to ensure accuracy of the data. However, computational averaging of the signals of one-color hybridizations from multiple independent samples is more straightforward. The choice between using one-color versus two-color methods depends on several factors, including the number of transcripts under examination, the need for speedy result and cost differences. Hence, one-color hybridizations are often more useful for surveying a large number of genes, while two-color hybridizations can be preferable for more sampling.

DETAILED DESCRIPTION

Figure 1:
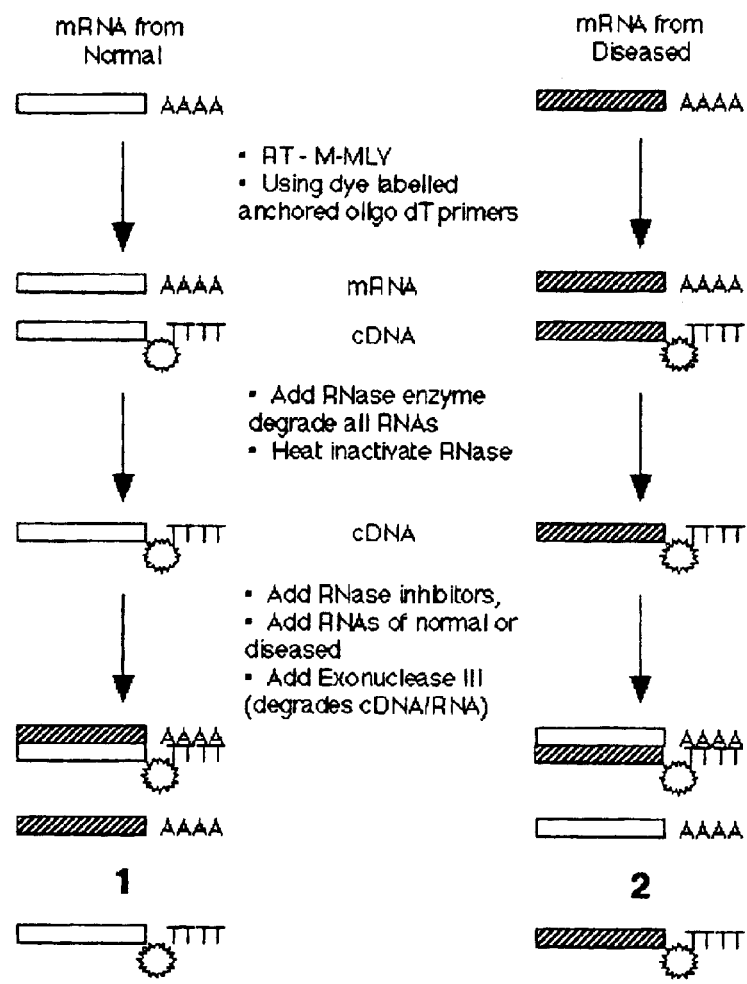
FIG. 1 is a schematic diagram illustrating the preferential display technique. The figure shows the end products of unique RNA and cDNA stands isolated after degradation of the cDNA/RNA complements.
Figure 2:
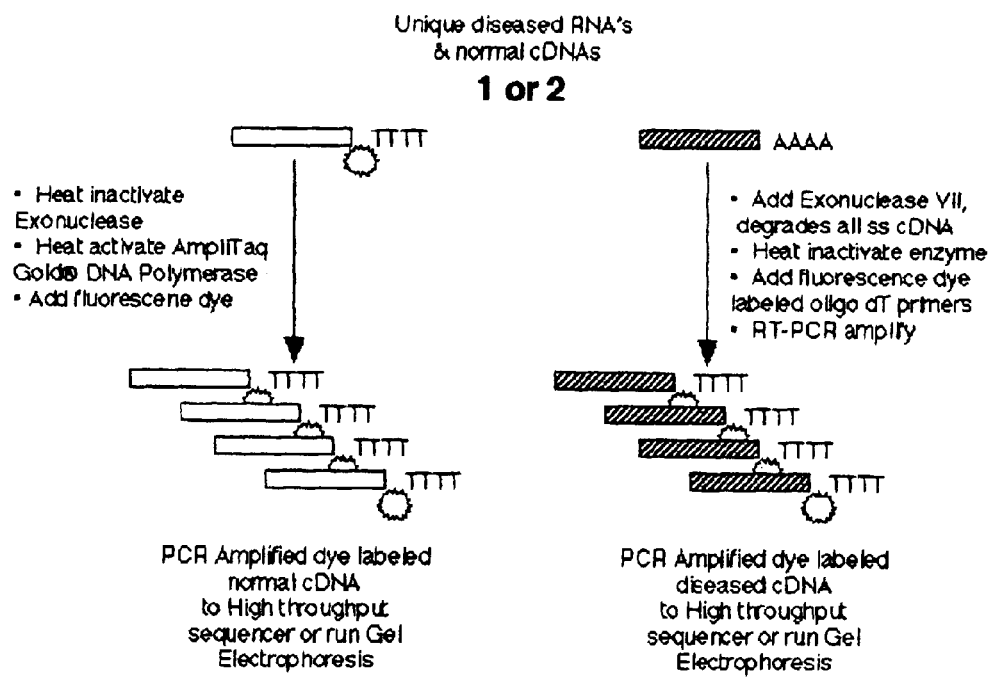
FIG. 2 is a schematic diagram of the final treatment with RNase to degrade the single stranded RNA's present in each sample and the PCR amplification of the isolated cDNA which are uniquely expressed in each sample.

The major problem in present gene expression technology is that too many genes are identified thus causing much wasted time and cost in sequencing redundant sequences found in both normal and diseased or diseased tissues. The method is a revolutionary differential gene display technology that provides a simplified, cost-effective method to efficiently identify and accurately isolate validated gene sequences between normal and diseased or diseased states of tissues. The method utilizes a combination of biomolecular chemistry methods to eliminate redundant sequences and fluorescence dye assay to identify unique sequences found in normal and/or diseased tissues. The method can be implemented in a single reaction tube, is amendable to miniaturization, and is extremely cost-effective which would be of benefit in toxicogenomic and drug discovery applications. It is estimated redundant sequences amounts to 98% of the total of all genes expressed in current display technologies.

The invention is a method called Preferential Display. The approach starts with the sample collection and categorizing of the cells, tissues or blood samples. Once the normalized control cells are isolated from the diseased state, expressed RNA's are isolated using standard methods. The RNA's are then placed into two tubes of normal and the other diseased RNA's for a total of four tubes. One normal and diseased are then RT-PCR with dye labeled oligos producing fluorescence labelled cDNA's in each tube. At this point of the reaction, RNA's of normal and diseased are added to their complementary tubes, normalized cDNAs with diseased RNAs and diseased cDNAs with normalized RNAs. Common sequences in each tube hybridize to form cDNA/RNA complements. The tubes are then treated with Exonuclease III or VII to degrade all the hybridized compliments. RNase is then added to digest the single stranded RNA's in each tube. The remaining undigested cDNA ar unique dye labeled sequences expressed in either normal or diseased states. Additional PCR can be ram to increase the cDNA present in each tube before running on a gel or high throughput sequencer.

The preferred embodiment of this invention begins with the Total RNA isolation and purification from cells/tissue using Totally RNA, RNA extraction kit from Ambion (Austin, Tex.). Reactions are carried out as per manufacturer's instructions.

RNA content is determined by adding 5 µl sample to 495 µl TE buffer and absorbance read at 260 nm. Concentration of RNA in µg/µl is determined by dividing absorbance at 260 nm by 0.025× (dilution factor). The average yield of RNA was 0.3 µg/µl. The major components that make up this invention includes the following materials.

---
Materials:
--- dH$_2$O
10X PCR Buffer (100 mM Tris-Cl, pH 8.4, 500 mM KCl, 15 mM, 15 mM MgCl$_2$ and 0.01% gelatin), GeneHunter Corporation ™, Nashville, TN
5X RT Buffer (125 mM Tris-Cl, pH 8.3, 188 mM KCl, 7.5 mM MgCl$_2$ and 25 mm DTT), GeneHunter Corporation ™, Nashville, TN
dNTP (250 µM) and (25 µM) GeneHunter Corporation ™, Nashville, TN ---
-continued Materials:
---

H-T$_{11}$M, where M could be G, A or C (2 µM), GeneHunter Corporation ™, Nashville, TN
H-APX, where X could be any arbitrary primer from 1 to 80 (2 µM), GeneHunter Corporation ™, Nashville, TN
MMLV Reverse Transcriptase (100 U/µl), GeneHunter Corporation ™
RNAse H (60 U/µl), diluted to 4 U/µl with TE buffer, Takara, Shiga, Japan
Taq DNA Polymerase (5 U/µl) Qiagen ™, Valencia, CA
Taq Polymerase Master Mix, Qiagen ™, Valencia, CA
Exonuclease III (65 U/µl), GibcoBRL ™ Life Technologies ™, Carlsbad, CA
Exonuclease VII (152 U/µl), GibcoBRL ™ Life Technologies ™, Carlsbad, CA
P$^{33}$ αATP (250 µCi), NEN ® Life Science Products, Boston, MA
cDNA (0.01 µg/µl)
RNA (0.1 µg/µl)

For the best mode of embodiment of the invention, the first step is the reverse transcription of mRNA from a total RNA pool. The Total RNA pool is obtained from mice heart and brain tissues provided by Clontech™, Palo Alto, Calif. Each preferential display reaction is preceded by an RNAse H incubation to eliminate the mRNA from the cDNA/mRnA complex that is obtained from the initial RT reaction. Once this is accomplished, the cDNA is ready to hybridize with the foreign mRNA that is introduced and that has some potions complementary to this cDNA.

EXAMPLE 1

Reverse Transcription Protocol

The Reverse Transcription protocol was obtained from the RNAimage kit manufactured by the GenHunter Corporation™, Nashville, Tenn.

| Component | Amount |
|---|---|
| dH$_2$O | 9.4 |
| 5X RT Buffer | 4.0 |
| dNTP (250 µM) | 1.6 |
| H-T$_{11}$M (2 µM) | 2.0 µl |
| Total RNA (0.1 µg/µl) | 2.0 µl |
| MMLV RT | 1.0 µl |

| Thermocycling Conditions for the RT Reaction |
|---|
| 65° C. for 5 minutes |
| 37° C. for 10 minutes |
| *Pause: Add MMLV RT Enzyme |
| 37° C. for 50 minutes |
| 75° C. for 5 minutes |
| Hold at 4° C. |

EXAMPLE 2

RNAase H Protocol

Following the RT reaction from Example 1, an RNAse H incubation is performed by adding 1.0 µl of RNAse H (4U/µl) to the 20 µl RT Reaction product:

| Component | Amount |
|---|---|
| dH$_2$O | 9.4 |
| 5X RT Buffer | 4.0 |
| dNTP (250 µM) | 1.6 |

-continued

| | |
|---|---|
| H-T$_{11}$M (2 μM) | 2.0 μl |
| cDNA/mRNA complex (0.01 μg/μl) | From 2.0 μl of total RNA (0.1 μg/μl) |
| MMLV RT | 1.0 μl |
| RNAse H | 1.0 μl |

At this point the foreign cDNA is ready to be mixed with the foreign RNA. For example, if brain cDNA is obtained, then heart RNA can be introduced and vice versa. Two different additional embodiments are used for this step depending on the enzyme utilized. The first embodiment is the Exonuclease III (digests dsDNA and portions of the DNA/RNA complex) embodiment and the other embodiment is the Exonuclease VII (digests ssDNA).

EXAMPLE 3

Exonuclease III Approach

| Component | Amount |
|---|---|
| dH$_2$O | 4.0 μl |
| 10X PCR Buffer | 0.8 μl |
| cDNA (RT) | 2.0 μl |
| RNA | 2.0 μl |
| Exonuclease III | 2.0 μl |

Thermocycling Conditions for the Exonuclease III Reaction

95° C. for 10 seconds
*Pause: Add RNA from foreign tissue
60° C. for 3 minutes
37° C. for 10 seconds
*Pause: Add Exonuclease III
37° C. for 30 minutes
95° C. for 10 minutes
Hold at 4.0° C.

EXAMPLE 4

Exonuclease VII Approach

| Component | Amount |
|---|---|
| DH$_2$O | 3.0 μl |
| 10x PCR Buffer | 1.0 μl |
| cDNA (RT) | 2.0 μl |
| RNA | 1.0 μl |
| Exonuclease VII | 1.0 μl |
| Rnase H (4 U/μl) | 0.5 μl |
| Taq Polymerase Master Mix | 13.0 μl |
| H-APX | 2.0 μl |

Thermocycling Conditions for Exonuclease VII Approach

95° C. for 10 seconds
*Pause: Add RNA
60° C. for 3 minutes
*Pause: Add H-APX and Taq Poly Master Mix
40° C. for 1 minute
30° C. for 10 seconds
*Pause: Add RNAse H
30° C. for 20 minutes
*Pause: Add Exonuclease VII
37° C. for 30 minutes
95° C. for 5 minutes
Hold at 4.0° C.

Regardless of the approach used, the product of the preferential display reactions is followed by a PCR with the following conditions:

EXAMPLE 5

PCR Theromcycling Protocol

Thermocycling Conditions for PCR Reaction

94° C. for 3 minutes
94° C. for 30 seconds
40° C. for 2 minutes
72° C. for 30 seconds
72° C. for 5 minutes
Hold at 4° C.

For the Exonuclease VII approach 0.2 μl of P$^{33}$ αATP, 2.0 μl of H-APX and H-T$_{11}$-M are added to the preferential display product prior to the PCR reaction.

The Exonuclease III approach does not require these components instead 2.0 μl of H-APX, 2.0 μl of H-T$_{11}$M, 0.2 μl of PxαATP, 1.6 μl of dNTP (25 μM), 1.2 μl of 10X PCR Buffer and 2.2 μl of dH$_2$O are added. These make a 20 μl total reaction volume for PCR Genes display is carried out using QuickPoint™ Gel system (Novex; San Diego, Calif.) Assay procedure is same as recommended by the manufacturer. Briefly, the precast gel is pre-electrophoresed for 5 minutes. 20 μl of PCR reaction mixed with an equal volume of QuickPoint™ sample loading buffer is then heated to 80° C. for 2 minutes and 1 μl is loaded immediately onto the gel (6% potyacrylaride). 0.5 μl of the sample loading buffer is loaded onto the remaining wells to assure a straight banding pattern. Electrophoresis is carried out in QuickPoint™ cell at 1200 V for approximately 10 minutes depending upon the length of the sequences. Following electrophoresis, the glass cassette enclosing the gel is washed in water for 5 minutes on a low speed shaker, dried in au oven at 80° C. for 20 minutes and exposed to X-ray film overnight to generate an autoradiogram.

The present invention has been described with reference to particular preferred embodiments; however, the scope of the invention is defined by the attached claims and should be construed to include reasonable equivalents.

What is claimed is:

1. A method for eliminating redundant sequences that are common between two samples, the method comprising of the steps:

isolating RNA strands from a first sample;
   isolating RNA strands from a second sample;
   generating cDNA strands from the RNA strands from the first sample;
   mixing the cDNA strands of the first sample with the RNA strands from the second sample;
   hybridizing the cDNA strands and RNA strands with common sequences to form cDNA/RNA complements, the cDNA strands and the RNA strands without common sequences remaining unhybridized cDNA strands and unhybridized RNA stands; and
   degrading the cDNA/RNA complements to leave the unhybridized cDNA strands and the unhybridized RNA strands.

2. The method of claim 1, wherein the step of generating cDNA strands from the RNA strands from the first sample comprises performing RT-PCR.

3. The method of claim 1, wherein the first sample is a healthy tissue and the second sample is a diseased tissue.

4. The method of claim 1, wherein the first sample is a diseased tissue and the second sample is a healthy tissue.

5. The method of claim 1, further comprising: amplifying the unhybridized cDNA stands using PCR.

6. The method of claim 1, further comprising: producing a second set of cDNA strands from the unhybridized RNA strands.

7. The method of claim 6, further comprising: amplifying the second set of cDNA strands using PCR.

8. The method of claim 1, wherein the step of degrading complements is performed with an Exonuclease III enzyme.

9. The method of claim 1, further comprising: displaying at least one of the unbridized cDNA strands and the unhybridized RNA strands.

10. The method of claim 1, wherein the step of displaying comprises using electrophoresis.

11. The method of claim 1, further comprising: reading at least one of the unhybridized cDNA strands and the unhybridized RNA strands with an autoradiogram.

12. The method of claim 1, wherein the first and second samples are selected from the group consisting of cells, tissues, pathogens, plants, and animals.

13. The method of claim 1, wherein the first and second sample are differentiated due to a diseased state, developmental change, or induced by an external or internal stimulus.

14. A method for determining differences between a first sample of cDNA strands and a second sample of RNA strands, the method comprising of the steps:

mixing the first sample of cDNA strands with the second sample of RNA strands;

hybridizing the cDNA strands and the RNA strands with common sequences to form cDNA/RNA complements, the cDNA strands and the RNA strands without common sequences remaining unhybridized cDNA strands and unhybridized RNA stands;

degrading the cDNA/RNA complements to leave the unhybridized cDNA strands and the unhybridized RNA strands; and analyzing at least one of the unhybridized cDNA strands and the unhybridized RNA strands to determine differences between the first sample and the second sample.

15. The method of claim 14, further comprising:

amplifying the unhybridized cDNA strands using PCR.

16. The method of claim 14, further comprising:

producing a further set of cDNA strands from the unhybridized RNA stands.

17. The method of claim 16, further comprising:

amplifying the further set of cDNA stands using PCR.

18. The method of claim 14, wherein the step of degrading complements is performed with an Exonuclease III enzyme.

* * * * *

UNITED STATES PATENT AND TRADEMARK OFFICE
CERTIFICATE OF CORRECTION

PATENT NO. : 6,861,219 B2
APPLICATION NO. : 09/961089
DATED : March 1, 2005
INVENTOR(S) : Iqbal et al.

It is certified that error appears in the above-identified patent and that said Letters Patent is hereby corrected as shown below:

On The Title Page:

In the References Cited section, please add:

Lennon, G.G. (2000) High-throughput gene expression analysis for drug discovery. DDT, 5(2), 59-66

Artinger, M. et al. (1998) High throughput Analysis of Differential Gene Expression. J. Cell. Biochem. Suppl. 30/31, 286-296

Berk, A.J. & Sharp, P.A. (1977) Sizing and mapping of early adenovirus mRNAs by gel electrophoresis of S1 endonuclease-digested hybrids. Cell 12, 721-732

Lee, J.J. and Costlow, N.A. (1987) A molecular titration assay to measure transcript prevalence levels. Methods Enzymol. 152, 633-648

Hedrick, S.M. et al. (1984) Isolation of cDNA clones encoding T cell-specific membrane-associated proteins. Nature 308, 149-153

Swaroop, A. et al. (1991) A simple and efficient cDNA library subtraction procedure: Isolation of human retina-specific cDNA clones. Nucleic Acids Res. 25, 1954

Lisitsyn, N. et al. (1993) Cloning the differences between two complex genomes. Science 259, 946-951

Greenberg, M.E. and Ziff, E.B. (1984) Stimulation of 3T3 cells induces transcription of the c-fos proto-oncogene. Nature 311, 433-438

Marzluff, W.F. (1978) Transcription of RNA in isolated nuclei. Methods Cell Biol. 19, 317-331

Manley, J.L. and Gefter, M.L. (1981) Transcription in mammalian genes in vitro. Gene Amplif. Anal. 2, 369-382

Liang, P. and Pardee, A.B. (1992) Differential display of eukaryotic messenger RNA by means of the polymerase chain reaction, Science 257, 967-997

UNITED STATES PATENT AND TRADEMARK OFFICE
CERTIFICATE OF CORRECTION

PATENT NO. : 6,861,219 B2
APPLICATION NO. : 09/961089
DATED : March 1, 2005
INVENTOR(S) : Iqbal et al.

It is certified that error appears in the above-identified patent and that said Letters Patent is hereby corrected as shown below:

Continued

In the References Cited section, please add:

Zhang, L. et al. (1997) Gene expression profiles in normal and cancer cells. Science 276, 1268-1272

Polyak, K. et al. (1997) A model for p53-induced apoptosis. Nature 389, 300-305

Schena M. et al. (1995) Quantitative monitoring of gene expression patterns with a complementary DNA microarray. Science 270, 467-470

Lennon, G.G. et al. (1996) the I.M.A.G.E. consortium: An integrated molecular analysis of genomes and their expression. Genomics 33, 151-152

Heller, R.A. et al. (1997) Discovery and analysis of inflammatory disease-related genes using cDNA microarrys. Proc. Natl. Acad. Sci. U.S.A. 95, 2150-2155

Schena, M. et al. (1996) Parallel human genome analysis: Microarray-based expression monitoring of 1000 genes. Proc. Natl. Acad. Sci. U.S.A. 93, 10614-10619

Gress, T. et al. (1992) Genome 3:609-619.

Southern, E.M. (1975) J. Mol. Biol. 98: 503-517.

Gray, N.S. et al. (1998) Exploiting chemical libraries, structure, and genomics in the search for kinase inhibitors. Science 281, 533-538

Marton, M.J. et al. (1998) Drug target validation and identification of secondary drug target effects using DNA microarrays. Nat. Med. 4, 1293-1301

Braxton, S. and Bedilion, T. (1994) The integration of microarray information in the drug development process. Curr. Opin. Biotechnol. 9, 643-649

UNITED STATES PATENT AND TRADEMARK OFFICE
CERTIFICATE OF CORRECTION

PATENT NO. : 6,861,219 B2
APPLICATION NO. : 09/961089
DATED : March 1, 2005
INVENTOR(S) : Iqbal et al.

It is certified that error appears in the above-identified patent and that said Letters Patent is hereby corrected as shown below:

In claim 5, line 2, please change the word "stands" to --strands--.

In claim 10, line 1, please change "method of claim 1," to --method of claim 9--.

In claim 14, line 10, please change the word "stands" to --strands--.

In claim 16, line 2, please change the word "stands" to --strands--.

In claim 17, line 2, please change the word "stands" to --strands--.

Signed and Sealed this

Nineteenth Day of September, 2006

JON W. DUDAS
*Director of the United States Patent and Trademark Office*